United States Patent
Benn

(10) Patent No.: US 7,110,572 B1
(45) Date of Patent: Sep. 19, 2006

(54) ANIMAL CARCASE ANALYSIS

(75) Inventor: Alan Benn, Maylands (AU)

(73) Assignee: RMS Research Management Systems Inc., (CA)

( * ) Notice: Subject to any disclaimer, the term of this patent is extended or adjusted under 35 U.S.C. 154(b) by 401 days.

(21) Appl. No.: 10/088,924

(22) PCT Filed: Sep. 20, 2000

(86) PCT No.: PCT/AU00/01147

§ 371 (c)(1),
(2), (4) Date: Mar. 19, 2002

(87) PCT Pub. No.: WO01/22081

PCT Pub. Date: Mar. 29, 2001

(30) Foreign Application Priority Data

Sep. 20, 1999 (AU) .................................... PQ2969

(51) Int. Cl.
G06K 9/00 (2006.01)
(52) U.S. Cl. ...................... 382/110; 382/162; 382/170
(58) Field of Classification Search ................ 382/110, 382/162–167, 170; 345/589–605; 358/538; 348/453

See application file for complete search history.

(56) References Cited

U.S. PATENT DOCUMENTS 4,745,472 A * 5/1988 Hayes ...................... 348/141

5,793,879 A * 8/1998 Benn et al. ................. 382/110

FOREIGN PATENT DOCUMENTS

DE 44 08 604 C 2 12/1995
DE PCT/DE99/01854 3/2000

* cited by examiner

Primary Examiner—Bhavesh M. Mehta
Assistant Examiner—Manav Seth
(74) Attorney, Agent, or Firm—Drummond & Duckworth

(57) ABSTRACT

The process for analyzing an ovine animal carcase comprises capturing an image of a dorsal view to generate color image data for the carcase (10). Predetermined anatomical points (21–24) of the carcase are identified to then derive dimensional measurements for the carcase. Also characterizing parameters such as yield and fat depth of the carcase are derived by processing color data included in the captured image data in conjunction with the derived dimensional measurements. The color data processed are the color data for predetermined selected surface areas, especially the chump, the loin and the shoulder areas (30–32) of the carcase (10) known or determined to have significant correlation to the characterizing parameter related to fatness. Desirably the tail (17) of the animal carcase is identified and its width determined since this is useful as a variable in a carcase yield predictive equation. The color data comprises average RGB values representing red, green and blue color components which are intensity normalized color values.

9 Claims, 4 Drawing Sheets

ANIMAL CARCASE ANALYSIS

FIELD OF THE INVENTION

This invention relates to methods and apparatus for analysing animal carcases, particularly for ovine carcase analyses.

BACKGROUND

In the meat industry, specialist trained and skilled operators are employed, in abattoirs for example, in order to inspect each animal carcase and to provide estimates or gradings of various parameters, such as the predicted saleable meat yield of each carcase. Such predictions of meat yield and gradings are very important for fixing a fair value for the carcase and for determining uses to which the carcase and meat cuts will be destined. Obviously it is very important for the meat industry generally including producers, processors and consumers that such operators are consistent both within a particular abattoir or processing facility and between different facilities at different places and different times.

In the case of ovine carcases, particularly sheep carcases, the analyses commonly used include both quantitative and qualitative measurements or assessments such as dimensional measurements, yield, particularly "lean meat yield", and fat depths.

There have been proposed and developed automated systems for image capture and colour analysis for automating beef carcase yield predictions or gradings, or at least for providing some objective replacement or supplement to human operators. However, such automated analysis and yield predicting systems for beef have not been applicable to sheep carcases both in their physical construction and arrangement, and also in the analyses performed and data output.

OBJECT OF THE INVENTION

It is an object of the present invention to provide a method and apparatus for analysis of animal carcases, particularly ovine animal carcases, so as to automatically derive quantitative and/or qualitative descriptors or characteristics of the carcases.

SUMMARY OF THE INVENTION

According to one aspect of the present invention there is provided a process for analysing an animal carcase which includes the steps of:

providing an image capture means for capturing image data relating to an animal carcase, presenting an animal carcase to the image capture means, the carcase being positioned with the dorsal view of the carcase presented directly to the image capture means, capturing image data for the dorsal view of the carcase by the image capture means, processing the image data so as to automatically identify predetermined anatomical points of the carcase, deriving dimensional measurements for the carcase by using the anatomical points identified, and deriving at least one characterising parameter related to fatness of the carcase by processing colour data included in the captured image data in conjunction with the derived dimensional measurements, the colour data processed being the colour data for at least one predetermined selected surface area of the carcase known or determined to have a significant correlation to the characterising parameter related to fatness.

According to another aspect of the present invention there is provided an apparatus for analysing an animal carcase, the apparatus including:

image capture means for capturing image data relating to an animal carcase, the image capture means including a colour camera located at an image capture station where an animal carcase is presented with the dorsal view of the carcase presented directly into the camera, the image capture means also including an associated system for converting the camera video signals to digital colour data signals, and processing means operative to automatically identify predetermined anatomical points of the carcase by processing the digital colour data signals, the processing means further being operative to derive dimensional measurements for the carcase using the anatomical points identified, the processing means further being operative to derive at least one characterising parameter related to fatness of the carcase by processing colour data included in the captured image data in conjunction with the derived dimensional measurements, the colour data processed being the colour data for at least one predetermined selected surface area of the carcase known or determined to have a significant correlation to the characterising parameter related to fatness.

It will be convenient to describe the invention in relation to analysis of a sheep carcase but it is to be understood that other animal carcases can be used with the present invention, particularly ovine carcases including, for example, goat carcases. The particular sheep carcase system developed and to be described herein can be generally similar to systems developed and published for analysing beef carcases, both in terms of equipment and software. Therefore reference may be made to such known systems for general features of the sheep carcase system. For example, patent specification WO 91/14180 describes and illustrates a beef carcase analysis system providing principal components and systems required for an automated analysis system.

As sheep carcases are typically less than half the length of beef carcases, however, the appropriate mechanical components, which generally means anything associated with the carcase imaging station can be scaled down. Individual components such as the camera and a camera enclosure (which preferably provides both physical protection and a controlled environment for the camera can be substantially the same as in the beef carcase systems.

The preferred apparatus has the image capture means which includes lighting means for illuminating the regions of the carcase in the region of the spine of the carcase where the predetermined selected surface areas of the carcase are located, the lighting means being positioned adjacent or distributed around the camera of the image capture means and directed generally towards the dorsal aspect of the carcase presented.

With regard to lighting of the sheep carcases as they are presented to the image capture means at the image capture station, it may be satisfactory to provide a single light source, e.g. adjacent to the camera, to illuminate each sheep carcase presented for image capture. A single light source may be suitable since wider or more uniform illumination may not be necessary to identify the anatomical points and since colour data used in the carcase analysis operation preferably relates to selected areas relatively close to the spine so that illumination from a single light source adjacent the camera may provide sufficient illumination for such areas. However it is also possible to use distributed lighting to give a flatter and more uniform light distribution.

Unlike beef carcases which are viewed as split sides with the lateral aspect presented to the camera, sheep carcases as mentioned earlier are imaged unsplit according to the present invention and are presented with the dorsal view, i.e. the back of the carcase, presented directly to the camera.

The analysis operations for sheep carcases are completely different to those for beef carcases, resulting in a completely different set of carcase measurements and descriptors and, of course, the derived outputs from the system are completely different and are appropriate to the description of sheep carcases.

The image capture station is designed to provide an environment to enable accurate, repeatable positioning, illumination and image capture of the sheep carcases. It is designed so that carcases moving on the normal abattoir carcase transport equipment progress unimpeded through an enclosure or booth and the images are automatically acquired. The carcase transport equipment preferably includes alignment devices operative to ensure the sheep carcases are positioned with the dorsal view presented directly at the camera. The enclosure also includes sensors to detect the presence of the carcases and control image capture.

The booth preferably includes its own lighting system to control the illumination of the carcase and the booth preferably excludes all external lighting so that external lighting does not illuminate the carcase. The lighting arrangement may use light source(s) positioned adjacent or distributed around the camera to illuminate the regions of the carcase which are useful for indicating carcase fatness and to help enhance the discrimination of fat and lean regions. Also included in the field of view are standard coloured tiles which are used to calibrate colour measurements by compensating for any changes in illumination or camera characteristics. The calibration procedures and apparatus can be substantially the same as used for beef carcase systems and, in particular, can be substantially as described in detail and illustrated in patent specification WO 98/39627.

For capturing the image data for each sheep carcase, the system preferably uses a video camera. The video camera is preferably enclosed in a temperature controlled enclosure and generates standard format video signals of the carcases which are provided to the controlling computer system. The camera and its enclosure can be substantially the same as used for a beef carcase system and may be for example as described in Australian patent specification No. PCT/AU00/00829, filed 10 Jul. 2000.

The image capture system including the camera and associated computer system may include a special interface card, known as a "frame grabber" to convert the camera video signals into a digital format. The image data will therefore comprise positional and colour data for each pixel in an array of pixels representing the imaged area. Once in a digital format, the sheep analysis software running on the computer system can process the image to detect features and make quantitative measurements.

The quantitative measurements can be generally grouped into two categories:
  (a) dimensional measurements, e.g. lengths, areas (including lengths and/or areas of the entire carcase or of particular components of the carcase such as the legs), ratios, angles, etc.,
  (b) colour measurements—for example each part of the captured image may be converted into three values, i.e. the RGB values representing the intensity of red, green and blue light coming from each respective part of the carcase. The absolute and relative values of these RGB numbers give a quantitative representation of the colour of the parts of the carcase. If desired, as described in patent specification No. PCT/AU00/00830 filed 10 Jul. 2000, the RGB values may be processed to provide intensity normalised colour values, i.e. colour values substantially independent of light intensity, so that subsequent analyses using these intensity normalised colour values are not subject to unwanted variations and inaccuracies due to differing light intensities of the illuminating light source(s).

The computer system would in practice also provide an operator interface for the overall system to enable control, configuration and display of results to an operator. Operator input can be via conventional peripheral devices such as via a computer mouse, keyboard, scanner, or via electronic links to other abattoir computer systems.

BRIEF DESCRIPTION OF THE DRAWINGS

To describe and illustrate the analysis procedures reference will be made to the accompanying drawings in which.

DETAILED DESCRIPTION OF PREFERRED EMBODIMENT

Figure 1:
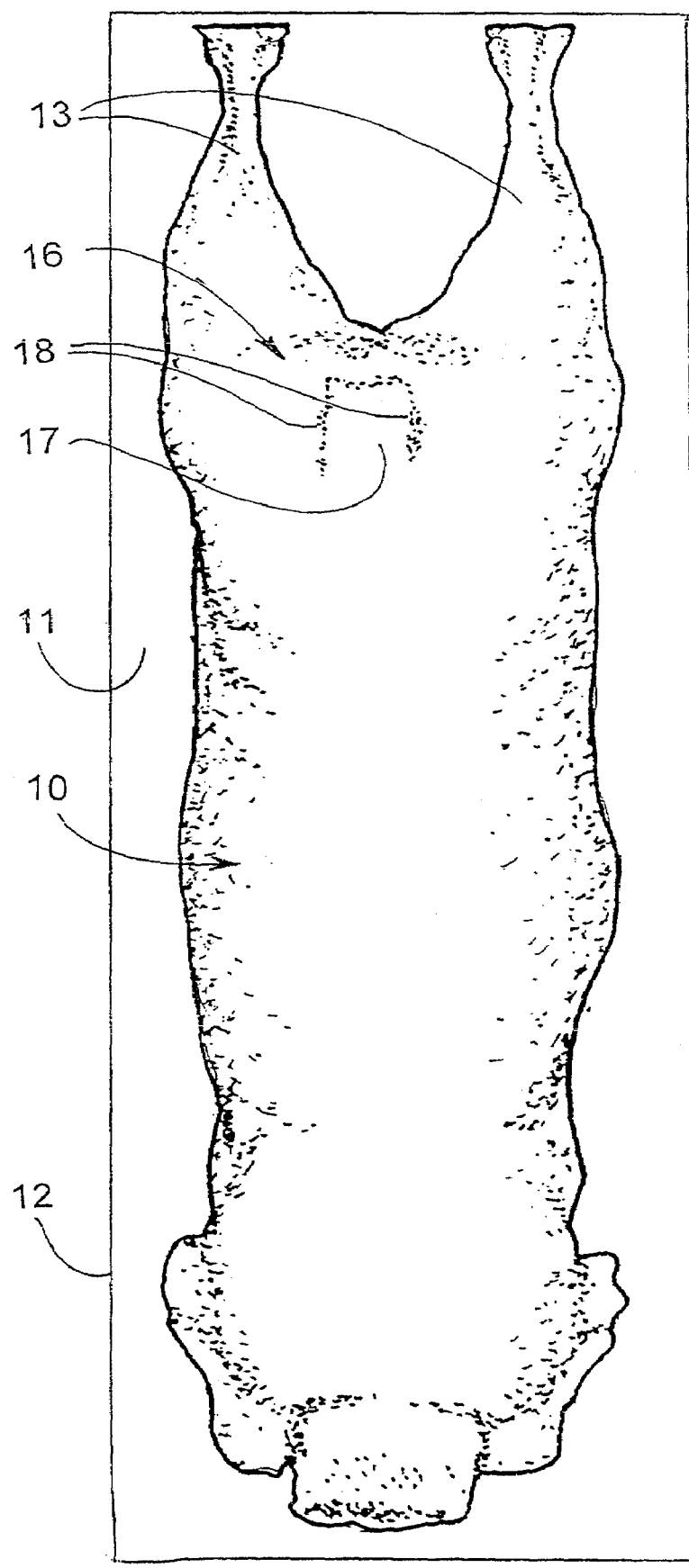
FIG. 1 shows a captured image of a sheep carcase suspended by the hind legs, e.g. from an overhead rail in a conventional transport system of an abattoir, the carcase having been presented to the camera with the dorsal view directly facing the camera.

As shown in the drawings, the captured image includes the image of the carcase 10 against a background 11. The background may comprise the image of a background panel such as a non-reflective black panel located behind the carcase in the image capture booth. The illuminated carcase overlying the black background 11 will enable ready processing of the image data to identify the outline 15 of the carcase image, e.g. by scanning inwardly from the edges 12 of the image through pixels representing the background 11 and identifying the boundary 15 by the abrupt change in colour and/or light intensity.

It may be possible for all dimensional measurements to be used in the system of the present invention to be measurements relating to the outline, i.e. with no features internal to this outline being located, identified and measured. However, if desired, the system may be programmed and operated to analyse captured image data in the area of the rump 16 of the animal so as to identify the tail 17. As seen in the drawings, the lateral edges of the tail 17 are delineated in the captured image by generally linear darker areas 18 extending lengthwise along each side of the tail so that these linear darker areas 18 can be identified by the analysis algorithms and hence the width of the tail 17 can be determined for use in yield prediction as mentioned later.

The main aims of the dimensional analysis are to find shape descriptors related to conformation/muscle score and also to locate features of the carcase to enable determination of the positions of predetermined areas for colour measurements and analysis.

Figure 2:
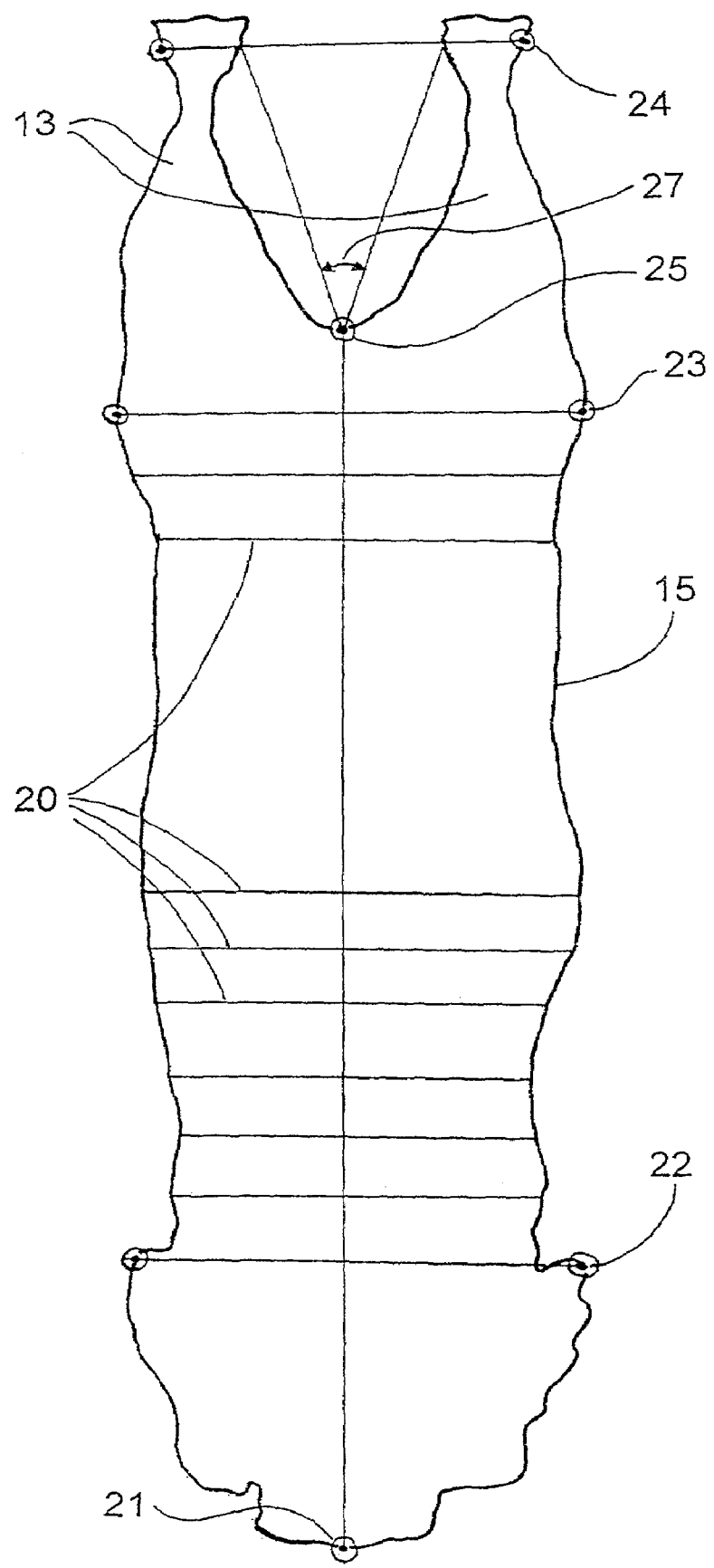
FIG. 2 is a depiction of the image of FIG. 1 having been analysed to identify and trace the carcase outline, to identify particular anatomical points, and to derive some dimensions.

FIG. 2 shows the results from locating the carcase outline 15 and the overlaid lines 20 illustrate basic dimensional measurements. All measurements are made with relation to detected "anatomical points". These are points on the outline 15 which are readily detected by features on the outline (e.g. sharp corners) and which are associated with particular parts of the anatomy. Examples are shown in FIG. 2 as the head point 21, "elbows" 22, hips 23, leg outer points 24, and the groin point 25. As well as simple linear distances as shown by the lines in FIG. 2, other measurements made may include: measurements of areas enclosed by the outline and various distance measurement lines 20; widths and areas on the hind legs 13 or portions thereof; and angles between distance measurement lines, e.g. the groin angle 27 between the lines from the groin point 25 to the hind legs 13. Another measurement mentioned earlier is the width of the tail 17 which has been found to have a significant predictive correlation to the yield of the carcase and which can therefore be used as a variable in a yield predictive equation.

The system may be calibrated so that dimensional measurements or distances 20 in the image can be converted to true distances/areas on the carcase by taking into account perspective or foreshortening effects of the dorsal view used. These and other dimensional measurements can been mathematically related to carcase descriptions provided by expert graders and also other quantitative measurements e.g. lean meat yield and fat depths, so that the measurements can be used to predict these other carcase descriptors in standardised manual carcase grading systems. Purely dimensional descriptors formerly provided by expert graders can be readily calculated from the dimensional data derived from the image analysis by relatively simple geometrical formulae or transformations. However, in deriving descriptors of the carcase such as lean meat yield, characteristics of the carcase in addition to purely dimensional characteristics are relevant and statistical methodologies can be used to derive predictive equations utilising both dimensional data as well as colour related data shown to have good predictive relationships or correlations with the descriptor being derived. An example of a purely dimensional characteristic having been determined to have good predictive correlations with yield is the width or thickness of the tail 17. Hence a derived measure of the width of the tail can be incorporated in a yield predictive equation.

Figure 3:
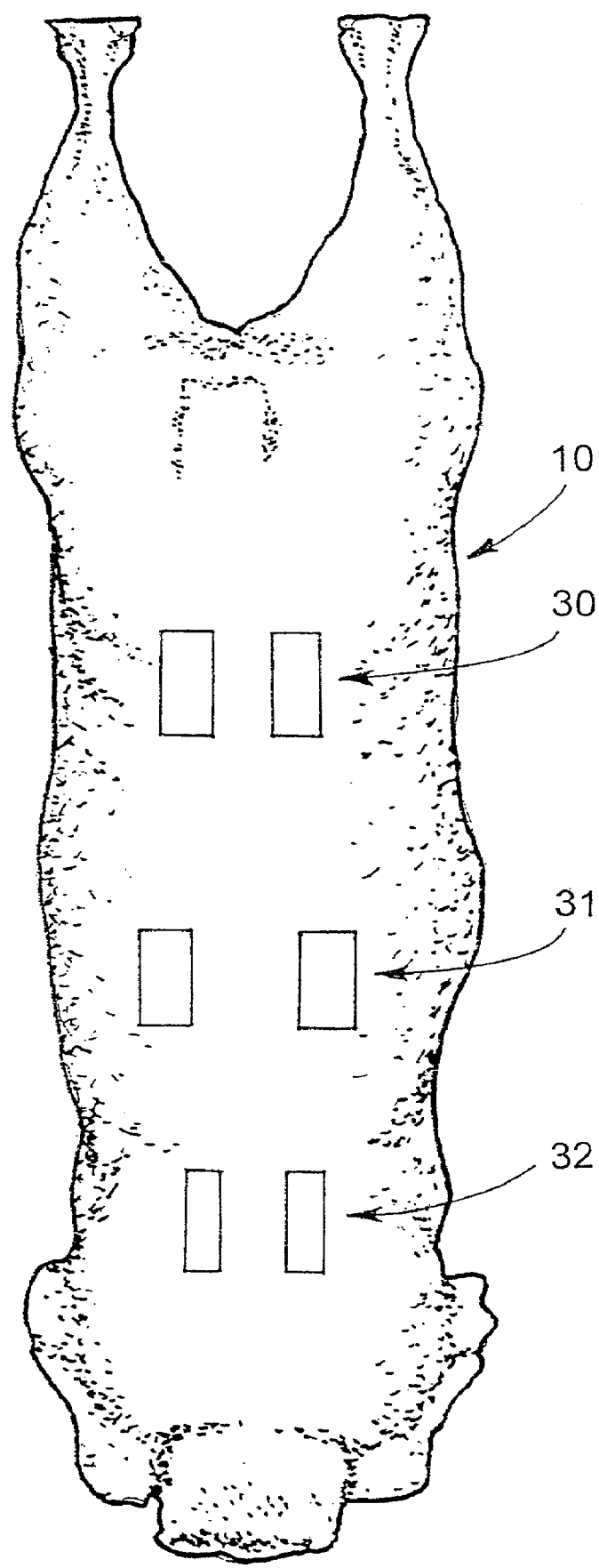
FIG. 3 is a similar view showing predetermined areas of the carcase identified for colour based analyses.

With regard to utilising colour information in the captured image data to derive descriptors of the sheep carcase, the simplest method of extracting colour information from the carcase image is to measure the average RGB values within a defined region. FIG. 3 shows rectangular areas superimposed on the carcase image. These rectangles have been automatically positioned relative to the anatomical features found in the dimensional analysis (FIG. 2) and are designed to coincide with chump 30, loin 31 and shoulder areas 32 that carcase grading experts use for evaluating carcase fatness. As illustrated, these areas 30–32 can be in respective pairs located symmetrically on opposite sides of the spine—enabling averaging of colour values for each laterally spaced pair, or possibly alarm or error signal generation if the average colour values for the two members of any pair vary significantly from each other, enabling manual intervention to identify the cause and correct for possible misleading output descriptors.

Relationships have been found by statistical analyses, e.g. multiple regression analyses, of multiple carcases to provide correlations between average RGB values and carcase fatness. Alternative a methods of using the RGB values to predict fatness may also be developed, e.g. analysing the rate of change of RGB values in a line profile across the carcase.

By discovering such relationships and providing the correlations to develop predictive equations, the present invention can provide a carcase analysis process and apparatus which automatically determines and outputs descriptors of the carcase, useful for example for grading and valuing the carcases. As mentioned earlier, dimensional descriptors are relatively easily derived and output once the outline and key anatomical points have been determined from the captured carcase images. Other carcase descriptors such as lean meat yield and fat thickness are correlated not only to dimensional characteristics but also to colour characteristics and therefore the predictive equations for such descriptors can be derived by statistical techniques using both dimensional and colour related parameters in the equations.

Figure 4:
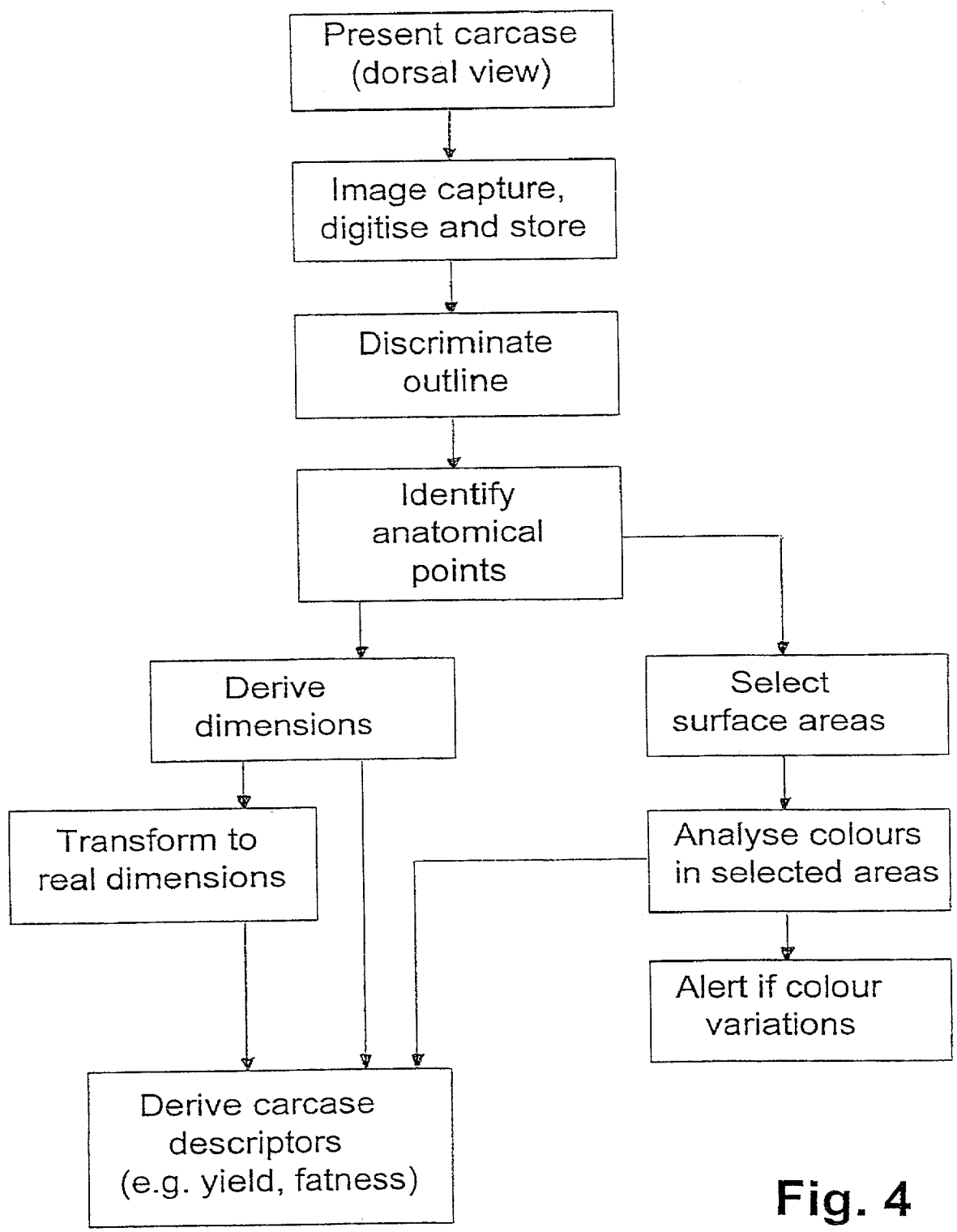
FIG. 4 is a flow chart showing the steps in the preferred process according to the present invention.

FIG. 4 illustrates process steps used in the processes according to the preferred embodiments of the present invention for image capture and analysis to provide characterising parameters for carcases. The steps can be readily understood by reference to the preceding description.

It will be seen from the preceding description that the present invention provides a useful process and apparatus for animal carcase analysis, particularly for ovine animal carcase analysis enabling at least partially automated analysis and output of useful carcase descriptors.

The invention claimed is:

1. A process for analysing an ovine animal carcase which includes the steps of:
    providing an image capture means for capturing image data relating to an ovine animal carcase,
    presenting an ovine animal carcase to the image capture means, the carcase being positioned with the dorsal view of the carcase presented directly to the image capture means,
    capturing image data for the dorsal view of the carcase by the image capture means, processing the image data so as to automatically identify predetermined anatomical points of the carcase,
    deriving dimensional measurements for the carcase by using the anatomical points identified, and
    deriving at lease one characterising parameter related to fatness of the carcase by processing colour data included in the captured image data in conjunction with the derived dimensional measurements, the colour data processed being the colour data for at least one predetermined selected surface area of the carcase known or determined to have a significant correlation to the characterising parameter related to fatness, wherein the process includes the further step of processing the image data to identify the tail of the ovine animal carcase, the identification of the tail comprising identification of lateral edges of the tail which are delineated in the captured image by generally linear darker areas extending lengthwise relative to the spine of the carcase, the process including the further step of determining the width of the tail between the lateral edges, and wherein the step of deriving at least one characterising parameter includes deriving a parameter related to the predicted yield of the carcase using the width of the tail as a variable in a carcase yield predictive equation.

2. A process as claimed in claim 1 wherein the step of processing colour data comprises measuring the average RGB values representing red, green and blue color components within said at least one predetermined selected surface area.

3. A process as claimed in claimed in claim 2 wherein the RGB values are intensity normalised colour values substantially independent of light intensity.

4. A process for analysing an ovine animal carcase which includes the steps of:
provBkVzbing an image capture means for capturing image data relating to an ovine animal carcase,
presenting an ovine animal carcase to the image capture means, the carcase being positioned with the dorsal view of the carcase presented directly to the image capture means,
capturing image data for the dorsal view of the carcase by the image capture means,
processing the image data so as to automatically identify predetermined anatomical points of the carcase,
deriving dimensional measurements for the carcase by using the anatomical points identified, and
deriving at least one characterising parameter related to fatness of the carcase by processing colour data included in the captured image data in conjunction with the derived dimensional measurements, the colour data processed being the colour data for at least one predetermined selected surface area of the carcase known or determined to have a significant correlation to the characterising parameter related to fatness, the step of processing colour data comprising measuring the average RGB values representing red, green and blue colour components within said at least one predetermined selected surface area,
wherein there are multiple predetermined selected surface areas of the ovine animal carcase for which colour data is processed, the multiple predetermined surface areas comprising areas which are automatically positioned relative to the predetermined anatomical points and which generally coincide with the chump, the loin and the shoulder areas of the ovine animal carcase used in standardised manual carcase grading systems for evaluating carcase fatness.

5. A process as claimed in claim 4 wherein the multiple surface areas are arranged in respective pairs locates symmetrically on opposite sides of the spine of the carcase, the processing of the coloured data including averaging of colour values for each laterally spaced pair of surface areas.

6. A process as claimed in claim 5 wherein the processing of colour data for the respective pairs of surface areas includes comparing the average colour values of each surface area with its respective counterpart of the respective pair and generating an alarm or error signal if the average colour values for the two members of any pair vary significant from each other.

7. A process for analysing an animal carcase which includes the steps of:
providing an image capture means for capturing image data relating to an animal carcase, presenting an animal carcase to the image capture means, the carcase being positioned with dorsal view of the carcase presented directly to the image capture means, capturing image data for the dorsal view of the carcase by the image capture means, processing the image data so as to automatically identify predetermined anatomical points of the carcase, deriving at least one characterising parameter related to fatness of the carcase by processing colour data included in the captured image date in conjunction with the derived dimensional measurements, the colour data processed being the colour data for at least one predetermined selected surface area of the carcase known or determined to have a significant correlation to the characterising parameter related to fatness, the step of processing colour data comprising measuring the average RGB values representing red, green and blue color components within said at least one predetermined selected surface area,
wherein the step of processing the colour data includes analysing the rate of change of RGB values in a line profile across the image of the carcase transverse to the longitudinal line of the spine and wherein the step of deriving a characterising parameter includes solving a predictive equation for a measure of fatness of the carcase in which the rate of change of the RGB values is a variable in that predictive equation.

8. A process for analysing an animal carcase which includes the steps of:
providing an image capture means for capturing image data relating to an animal carcase, presenting an animal carcase to the image capture means, the carcase being positioned with the dorsal view of the carcase presented directly to the image capture means, capturing image data for the dorsal view of the carcase by the image capture means, processing the image data so as to automatically identify predetermined anatomical points of the carcase,
deriving dimensional measurements for the carcase by using the anatomical points identified, and
deriving at least one characterising parameter related to fatness of the carcase by processing colour data included in the captured image data in conjunction with the derived dimensional measurements, the colour data processed being the colour data for at least one predetermined selected surface area of the carcase known or determined to have a significant correlation to the characterising parameter related to fatness, the step of processing colour data comprises measuring the average RGB values representing red, green and blue colour components within said at least one predetermined selected surface area,
wherein the step of deriving a characterising parameter related to fatness of the carcase includes performing statistical analyses of multiple carcases to provide correlations between average RGB values of said at least predetermined selected surface area and carcase fatness and using these correlations to develop a predictive equation for carcase fatness in which the average RGB values are variables in the predictive equation.

9. A process as claimed in claim 8 wherein the parameter related to fatness of the carcase is selected from lean meat yield and fat thickness.

* * * * *